(12) United States Patent
Cho

(10) Patent No.: US 10,864,319 B2
(45) Date of Patent: Dec. 15, 2020

(54) BALLOON INFUSER

(71) Applicant: CEBIKA INC., Uiwang-si (KR)

(72) Inventor: Byoung Chic Cho, Seongnam-si (KR)

(73) Assignee: CEBIKA INC., Uiwang-si (KR)

( * ) Notice: Subject to any disclaimer, the term of this patent is extended or adjusted under 35 U.S.C. 154(b) by 298 days.

(21) Appl. No.: 15/742,485

(22) PCT Filed: May 17, 2016

(86) PCT No.: PCT/KR2016/005210
§ 371 (c)(1),
(2) Date: Jan. 5, 2018

(87) PCT Pub. No.: WO2017/007123
PCT Pub. Date: Jan. 12, 2017

(65) Prior Publication Data
US 2018/0200427 A1    Jul. 19, 2018
US 2019/0201616 A9    Jul. 4, 2019

(30) Foreign Application Priority Data

Jul. 8, 2015 (KR) .......................... 10-2015-0097206
Jul. 8, 2015 (KR) .......................... 10-2015-0097207
Jul. 8, 2015 (KR) .......................... 10-2015-0097208

(51) Int. Cl.
*A61M 5/152* (2006.01)
*A61M 5/148* (2006.01)
*A61M 5/142* (2006.01)

(52) U.S. Cl.
CPC ............ *A61M 5/152* (2013.01); *A61M 5/142* (2013.01); *A61M 5/148* (2013.01); *A61M 2205/3389* (2013.01); *A61M 2205/583* (2013.01)

(58) Field of Classification Search
CPC ...... A61M 5/152; A61M 5/142; A61M 5/148; A61M 2205/583; A61M 2205/3389; A61M 39/10
See application file for complete search history.

(56) References Cited

U.S. PATENT DOCUMENTS 3,895,631 A    7/1975 Buckles et al.
4,201,207 A    5/1980 Buckles et al.
(Continued)

FOREIGN PATENT DOCUMENTS

CN    102935252 A    2/2013
JP    56-102252       8/1981
(Continued)

OTHER PUBLICATIONS

Extended European Search Report for application No. 16821529.1, dated Jan. 18, 2019.

*Primary Examiner* — Brandy S Lee
*Assistant Examiner* — Nidah M Hussain
(74) *Attorney, Agent, or Firm* — Squire Patton Boggs (US) LLP

(57) ABSTRACT

The present invention relates to a medical instrument, and more particularly, to a balloon infuser. The balloon infuser includes an upper cover (10) in which a scale mark (13) including linear scales is displayed, a lower cover (20) fixed to a lower side of the upper cover (10), a flexible expandable member (70) located inside the upper cover (10) and in which contents are accommodated, and an elevation part (30) elevated according to an expansion degree of the expandable member (70) and having a scale indication line (34) on one surface thereof, the scale indication line (34) indicating the scale mark (13).

11 Claims, 17 Drawing Sheets

(56) References Cited

U.S. PATENT DOCUMENTS

| | | | | |
|---|---|---|---|---|
| 4,318,400 | A | * | 3/1982 | Peery ................... A61M 5/152 604/18 |
| 5,120,315 | A | * | 6/1992 | Hessel .................. A61M 5/152 128/DIG. 12 |
| 5,178,610 | A | * | 1/1993 | Tsujikawa ............. A61M 5/152 128/DIG. 12 |
| 6,024,724 | A | * | 2/2000 | Lee ....................... A61M 5/152 604/132 |
| 8,109,907 | B2 | | 2/2012 | Tsukada et al. |
| 2009/0208811 | A1 | * | 8/2009 | Nakamura .............. F17C 13/04 429/404 |
| 2014/0155829 | A1 | | 6/2014 | Oh |

FOREIGN PATENT DOCUMENTS

| | | |
|---|---|---|
| JP | 2568589 B2 | 10/1996 |
| JP | 11-9689 | 1/1999 |
| JP | 3126979 B2 | 1/2001 |
| JP | 2001-157710 A | 6/2001 |
| JP | 2003-111839 | 4/2003 |
| KR | 10-1999-0006264 A | 1/1999 |
| KR | 10-2008-0092047 A | 10/2008 |
| KR | 10-1535947 B1 | 7/2015 |

\* cited by examiner

BALLOON INFUSER

TECHNICAL FIELD

The present invention relates to a medical instrument, and more particularly, to a balloon infuser.

BACKGROUND ART

A balloon infuser, also called a balloon infusion pump or a portable infusion pump (PIP), is a disposable medicine infusion instrument that is used to continuously infuse a medicine, such as an antitumor agent, of which an amount and an infusion speed are important, at a constant speed. It is general to use the balloon infuser after a separate speed adjusting device is coupled to the balloon infuser.

The balloon infuser is safe and sanitary from external factors, may be conveniently carried so that a separate power source is not necessary, and does not influence everyday lives, and accordingly, the studies and demands thereof have been increased outpatient treatments are possible without the patient who requires continuous infusion of medicines having to be hospitalized.

However, the currently used general balloon infuser has the following problems.

Because the expansion degree of a balloon follows the amount of contents included in the balloon, it is difficult to accurately set the amount of contents. The user has to determine how many contents are left in the balloon infuser and how many contents are exhausted in the balloon infuser by estimating the expansion degree of the balloon by naked eyes. Although a balloon infuser in which an arc-shaped scale mark is printed on an outer housing so that the amount of the left contents may be informed by indicating the arc-shaped scale mark, it is difficult to accurately indicate a curvature of a distal end of the balloon according to the contraction degree of the balloon, making it impossible to solve the problem.

Further, it is also problematic to use an adhesive because it is important to seal the balloon infuser while employing a plurality of components to discharge a fixed quantity of contents. Accordingly, the use of an adhesive makes the manufacturing process difficult, and increases manufacturing costs and is not desirable in aspect of sanitation.

It is difficult to completely discharge contents left while the balloon is almost completely contracted and few contents are left to discharge the contents with a contraction force of the balloon. Accordingly, the use of the balloon is terminated and discarded in the state in which the contents are partially left on the discharge passage. A space in which the contents which are not discharged is left is called a dead space, and the dead space is considerably present in the general balloon infuser. The presence of the dead space economically burdens the user.
US 2014-0155829
CN 102935252

DISCLOSURE

Technical Problem

The present invention is adapted to solve the problems.
The present invention provides a balloon infuser that may accurately indicates the amount of contents left in a balloon infuser, may allow firm coupling without using an adhesive, and may maximally decrease the amount of a dead space.

Technical Solution

In accordance with an aspect of the present invention, there is provided a balloon infuser including an upper cover (10) in which a scale mark (13) including linear scales is displayed, a lower cover (20) fixed to a lower side of the upper cover (10), a flexible expandable member (70) located inside the upper cover (10) and in which contents are accommodated, and an elevation part (30) elevated according to an expansion degree of the expandable member (70) and having a scale indication line (34) on one surface thereof, the scale indication line (34) indicating the scale mark (13).

Further, the balloon infuser further include an upper connector holder (40) coupled to an upper elevation part opening (31) located on an upper side of the elevation part (30), an upper connector (50) coupled to the upper connector holder (40), an inner shaft (60) coupled to the upper connector (50), a lower connector holder (100) coupled to a lower opening (21) of the lower cover (20), a lower connector (90) coupled to the lower connector holder (100), and an outer shaft (80) coupled to the lower connector (90).

Further, the expandable member (70) may cover the inner shaft (60) such that the inner shaft (60) is sealed, and a hollow part (88) may be located in the outer shaft (80), and the inner shaft (60) may be inserted into the hollow part (88) to be elevated through a slide movement.

Further, an infusion opening (81) communicating with the lower opening (21) may be located at a central portion of the outer shaft (80), the infusion opening (81) communicates with the hollow part (88) through an infusion hole (82), a plurality of infusion holes (83, 84) are located in the hollow part (88), the plurality of infusion holes (83, 83) are seated from the outside by the expandable member (70), and if contents are infused through the infusion opening (81), the infused contents are introduced into the hollow part (88) through the infusion hole (82) and are discharged into the expandable member (70) through the plurality of infusion holes (83, 84) to expand the expandable member (70) and lifting the inner shaft (60).

Further, the upper elevation part opening (31) and the lower opening (21) may have the same shape and are formed in 180 degree opposite directions, the upper connector holder (40) coupled to the upper elevation part opening (31) and the lower connector holder (100) coupled to the lower opening (21) may be the same component, and the upper connector (50) and the lower connector (90) may be the same components.

Further, the upper connector holder (40) may be snap-coupled in the upper elevation part opening (31) without using an adhesive, the upper connector holder (40) and the upper connector (50) may be snap-coupled to each other without using an adhesive, and the expandable member (70) may be located between the upper connector (50) and the inner shaft (60) to be sealed without using an adhesive, and the lower connector holder (100) may be snap-coupled in the lower opening (21) without using an adhesive, the lower connector holder (100) and the lower connector (90) may be snap-coupled to each other without using an adhesive, and the expandable member (70) may be located between the lower connector (90) and the outer shaft (80) to be sealed without using an adhesive.

Further, an upper side of the inner shaft (60) may be coupled to the upper connector (50), the shapes of inner wall bodies (65, 66, 67) of the inner shaft (60) may correspond to the shapes of outer wall bodies (55, 56, 57) of the upper connector (50), and the expandable member (70) may be located between the inner wall bodies (65, 66, 67) and the outer wall bodies (55, 56, 57).

Further, any one inner wall body (66) of the inner wall bodies (65, 66, 67) and any one outer wall body (56) corresponding to the any one inner wall body (66) are inclined with respect to the other inner wall bodies (65, 67) and the other wall bodies (55, 57), and a protrusion (58) protruding inwards may be located on another outer wall body (57) of the outer wall bodies (55, 56, 57), and the protrusion (58) presses the expandable member (70).

Further, a pair of upper connector holder stopping steps (32) and a pair of upper connector holder supports (33) may be radially located along a border of the upper elevation part opening (31), and an upper connector stopping step (42) and an elevation part support (43) may be located radially along an outer periphery of the upper connector holder (40), and an upper connector holder seating part (32*a*) protruding inwards may be located at a distal end of a lower side of the upper connector holder stopping step (32), and an elevation part seating part (43*a*) protruding outwards may be located at a distal end of a lower side of the elevation part support (43).

Further, a downward movement of the upper connector holder (40) may be restricted by locating the upper connector holder seating part (32*a*) below the upper connector stopping step (42) and an upward movement of the upper connector holder (40) may be restricted by locating the elevation part seating part (43*a*) below the upper connector holder support (33).

Further, an upper connector holder coupling part (52) protruding outwards may be located at a distal end of an upper side of the upper connector (50), and an upper connector shoulder (53) protruding outwards may be located at a distal end of a lower side of the upper connector (50), and a downward movement of the upper connector (50) may be restricted by locating the upper connector stopping step (42) below the upper connector holder coupling part (52) and an upward movement of the upper connector (50) may be restricted by locating the upper connector shoulder (53) below the elevation part seating part (43*a*).

Further, the plurality of infusion holes (83, 84) may include a pair of upper infusion holes (83) located at a central portion of the hollow part (88), and a pair of lower infusion holes (84) located below the hollow part (88).

Further, the height of the upper infusion hole (83) may correspond to the central height of the expansion member (70) in a maximally expanded state.

Advantageous Effects

According to the present invention, the amount of contents left in the balloon infuser may be accurately indicated. An accurate amount of left contents may be informed of the user by employing a separate member such as the elevation part, providing a scale indication line to a distal end of the elevation part, printing a linear scale mark in the outer housing, and synchronizing expansion and contraction of the balloon such that the elevation part is elevated.

Further, the balloon may be firmly fixed without using a separate adhesive. Moreover, because the connector and the connector holder are the same component, manufacturing costs may be lowered by changing the directions of the upper side and the lower side of the balloon infuser after production.

The finished product may be manufactured only through simple snap-coupling of injection-molded components, the process may be easy, the manufacturing time may be reduced, and defect rates may be significantly reduced.

Further, the amount of used contents included in the balloon infuser may be improved by reducing the dead space, the economic gains of the user may be secured, and a prescription may be allowed by accurately predicting the amount of a medicine.

DESCRIPTION OF THE INVENTION

Figure 10:
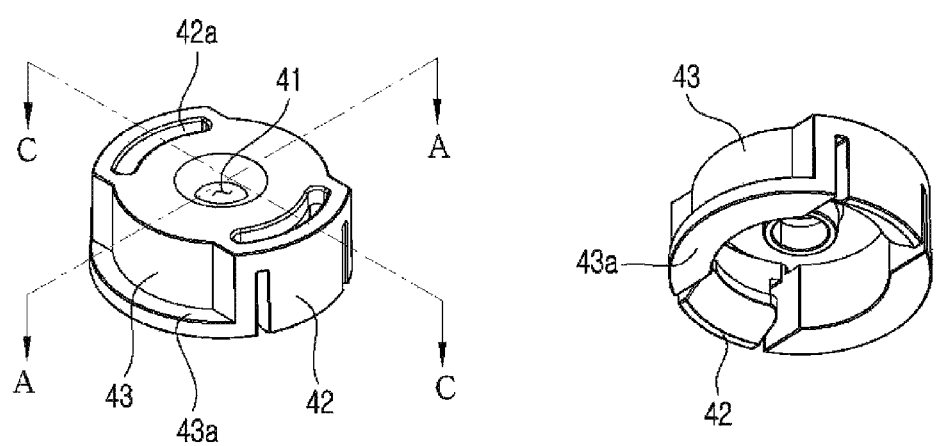
FIG. 10 is referenced.
Figure 11:
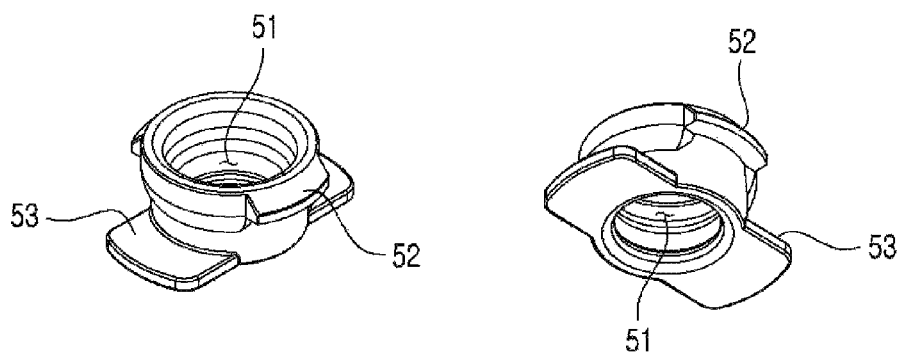
Figure 12:
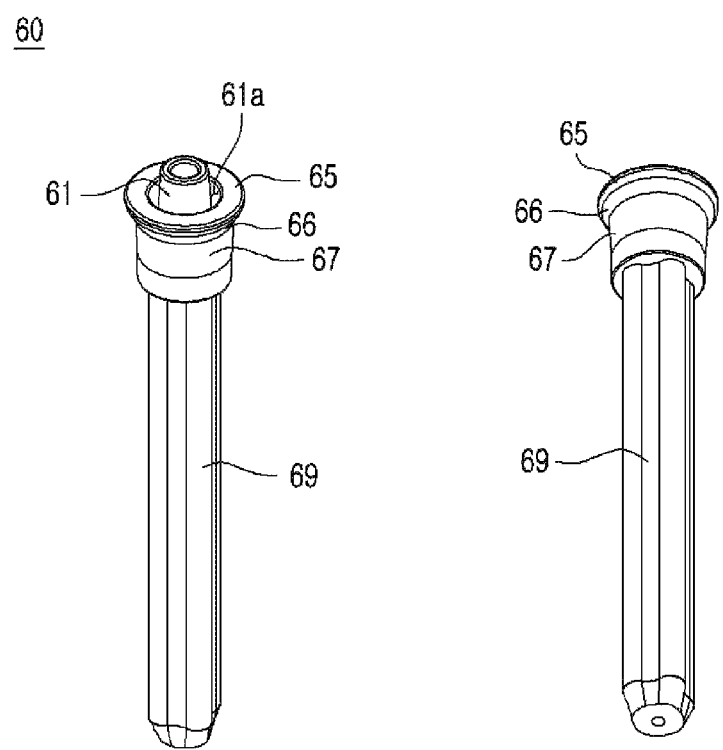
Figure 13:
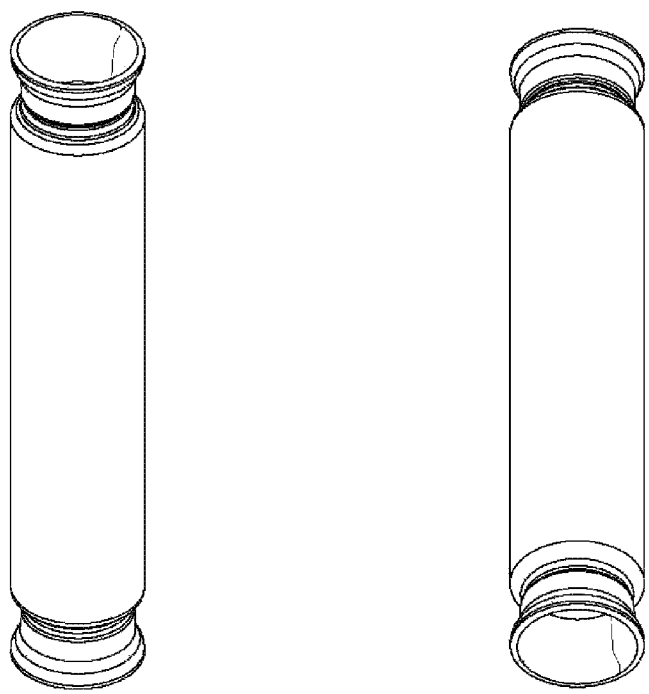
Figure 14:
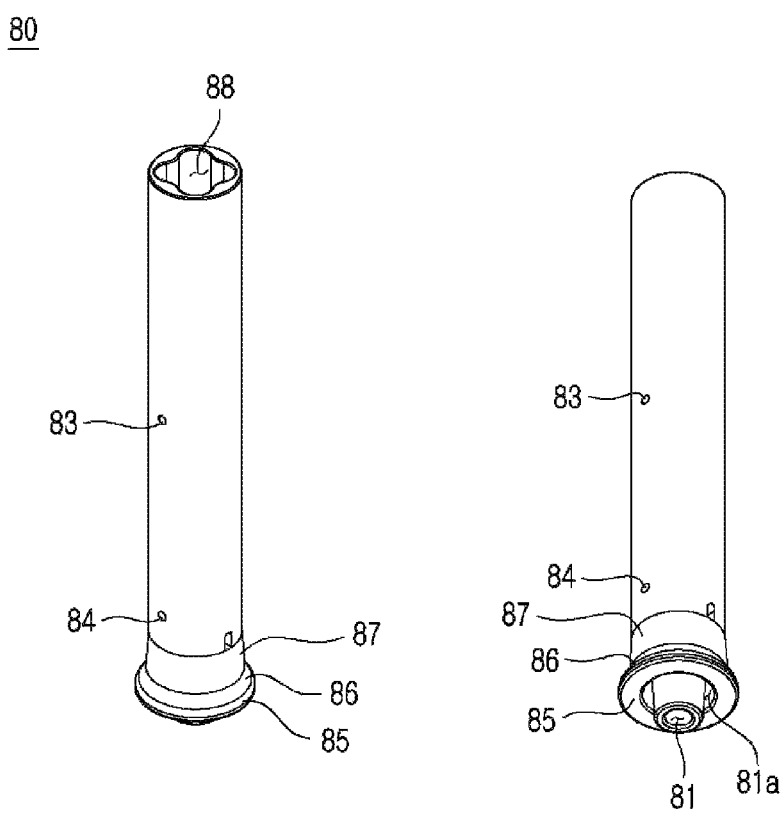
Figure 15:
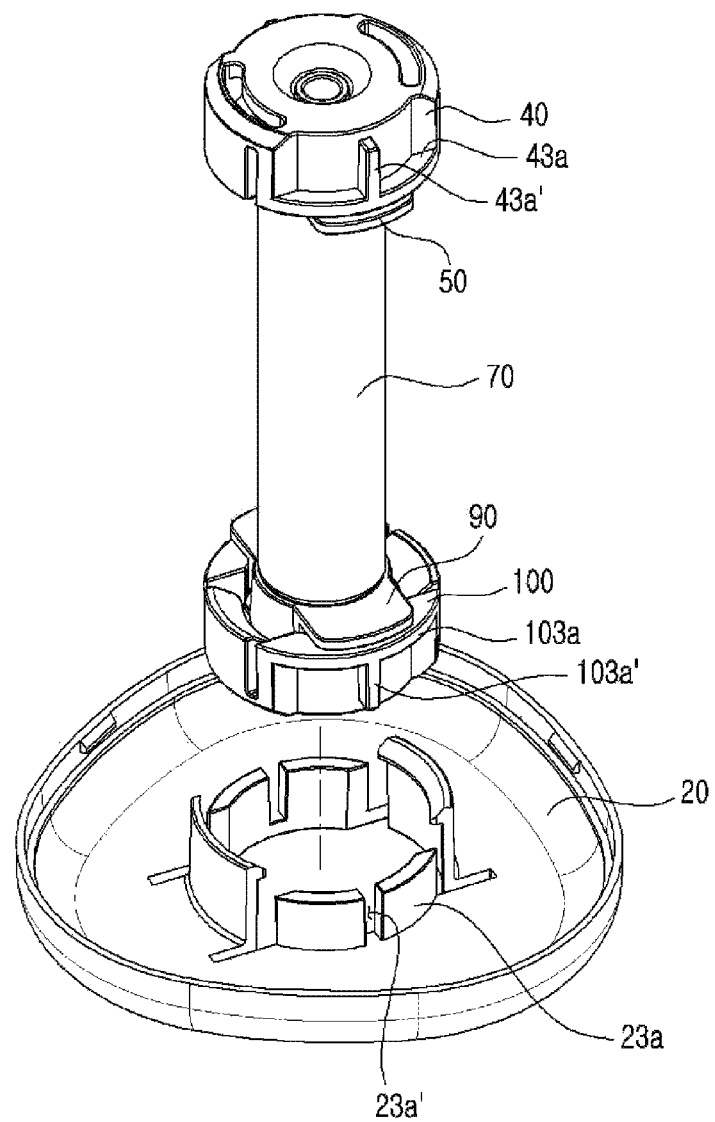

FIG. 10 illustrates perspective views of an upper connector holder 40 of the balloon infuser according to the present invention. For description, a top perspective view and a bottom perspective view are illustrated together. A lower connector holder 100 also has the same shape;

FIG. 11 illustrates perspective views of an upper connector 50 of the balloon infuser according to the present invention. For description, a top perspective view and a bottom perspective view are illustrated together. A lower connector 90 also has the same shape;

FIG. 12 is an exploded perspective view of an inner shaft 60 of the balloon infuser according to the present invention. For description, a top perspective view and a bottom perspective view are illustrated together;

FIG. 13 illustrates perspective views of an expansion member 70 of the balloon infuser according to the present invention. For description, a top perspective view and a bottom perspective view are illustrated together. As will be described below, it is noted that the shape of the expandable member 70 may vary because the expandable member 70 is an expandable flexible member;

FIG. 14 is an exploded perspective view of an outer shaft 80 of the balloon infuser according to the present invention. For description, a top perspective view and a bottom perspective view are illustrated together; and FIG. 15 illustrates a balloon infuser according to another embodiment of the present invention, and for description, the elevation part 30 and the upper cover 10 are omitted.

BEST MODE

The present invention relates to a balloon infuser that is a medical instrument. It is said in advance that the present invention is not a treatment method in which a human body is not a direct target.

Hereinafter, it is noted that the "contents" are medical fluids, such as chemicals, which are infused into the balloon infuser according to the present invention.

Figure 3A:
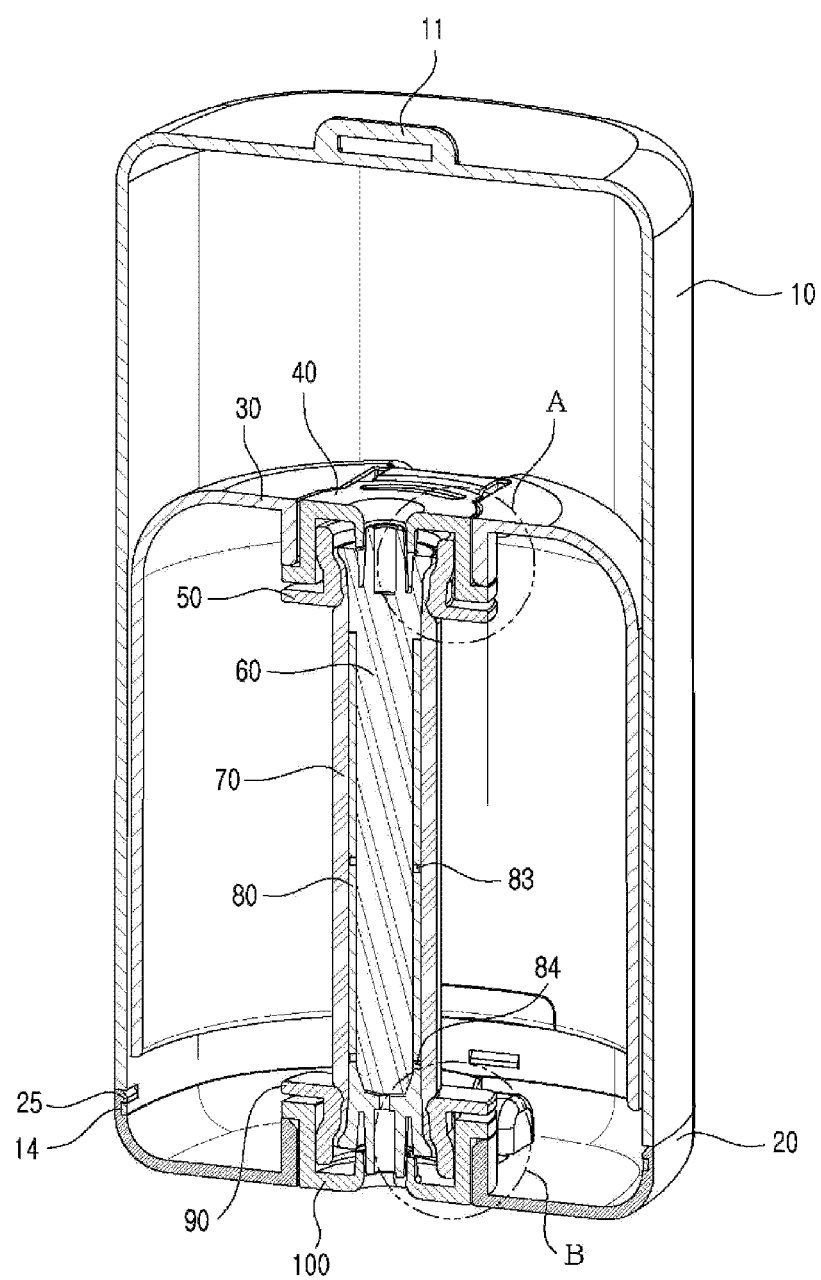
FIG. 3A is a sectional perspective view before contents are infused into the balloon infuser according to the present invention, and is a sectional view viewed from direction A-A when
Figure 3B:
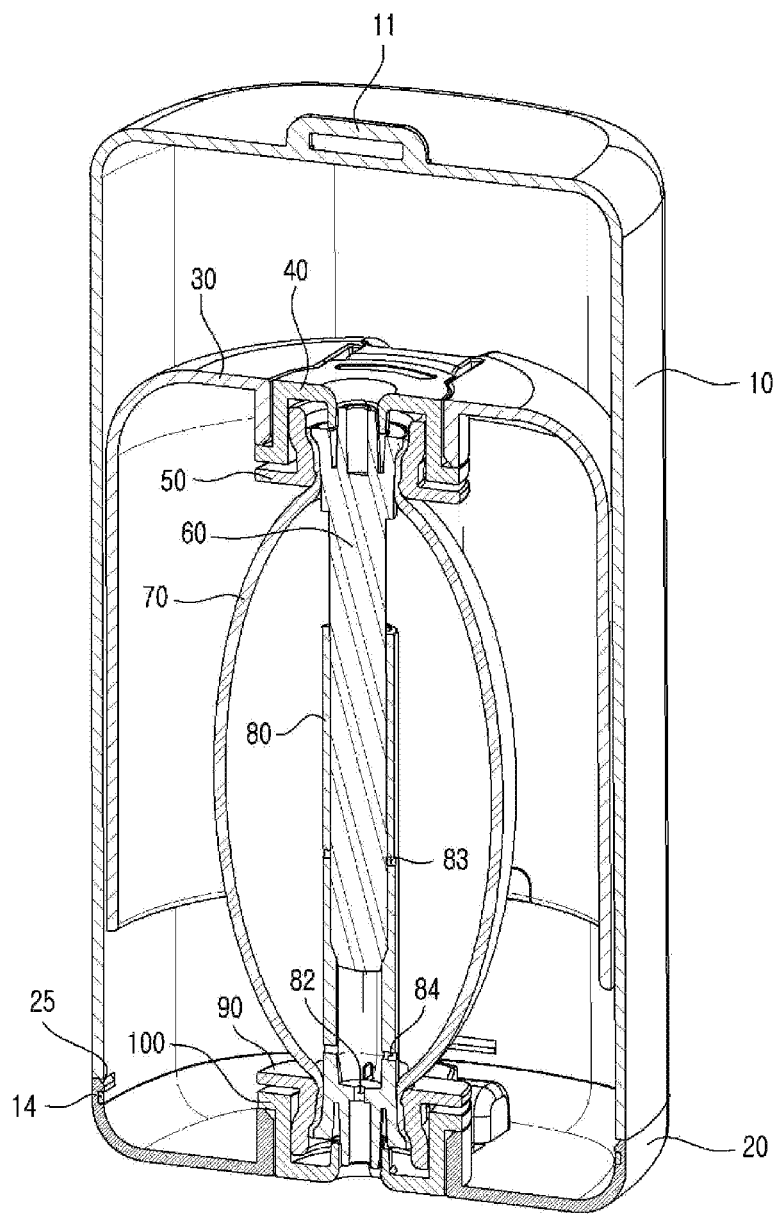
FIG. 3B is a sectional perspective view while contents are infused into the balloon infuser according to the present invention or when approximately half of the contents are used after the contents are infused, and is a sectional view viewed form direction A-A when
Figure 3C:
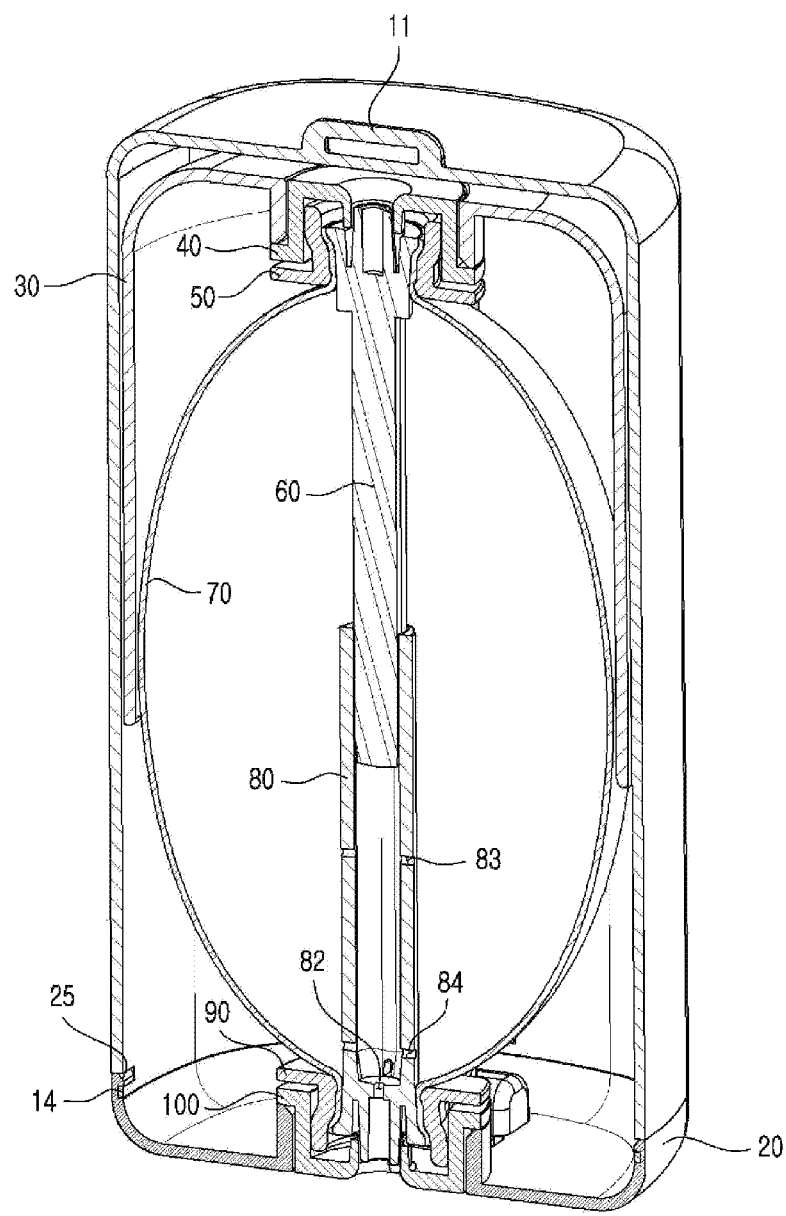
FIG. 3C is a sectional perspective view in a state in which contents are completely infused into the balloon infuser according to the present invention, and is a sectional view viewed along direction A-A when

Hereinafter, for description, an upper side of FIGS. 3A to 3C is referred to as an upper side and a lower side of FIGS. 3A to 3C is referred to as a lower side. Further, for description, a direction that faces the central axis of the balloon infuser is referred to as an inward direction and an opposite direction thereof is referred to as an outward direction.

Hereinafter, the present invention will be described in detail with reference to the accompanying drawings.

1. DESCRIPTION OF WHOLE STRUCTURE

As illustrated in FIGS. 1A to 1D, various embodiments of the balloon infuser according to the present invention are possible according to the form of the upper cover 10.

Figure 1:
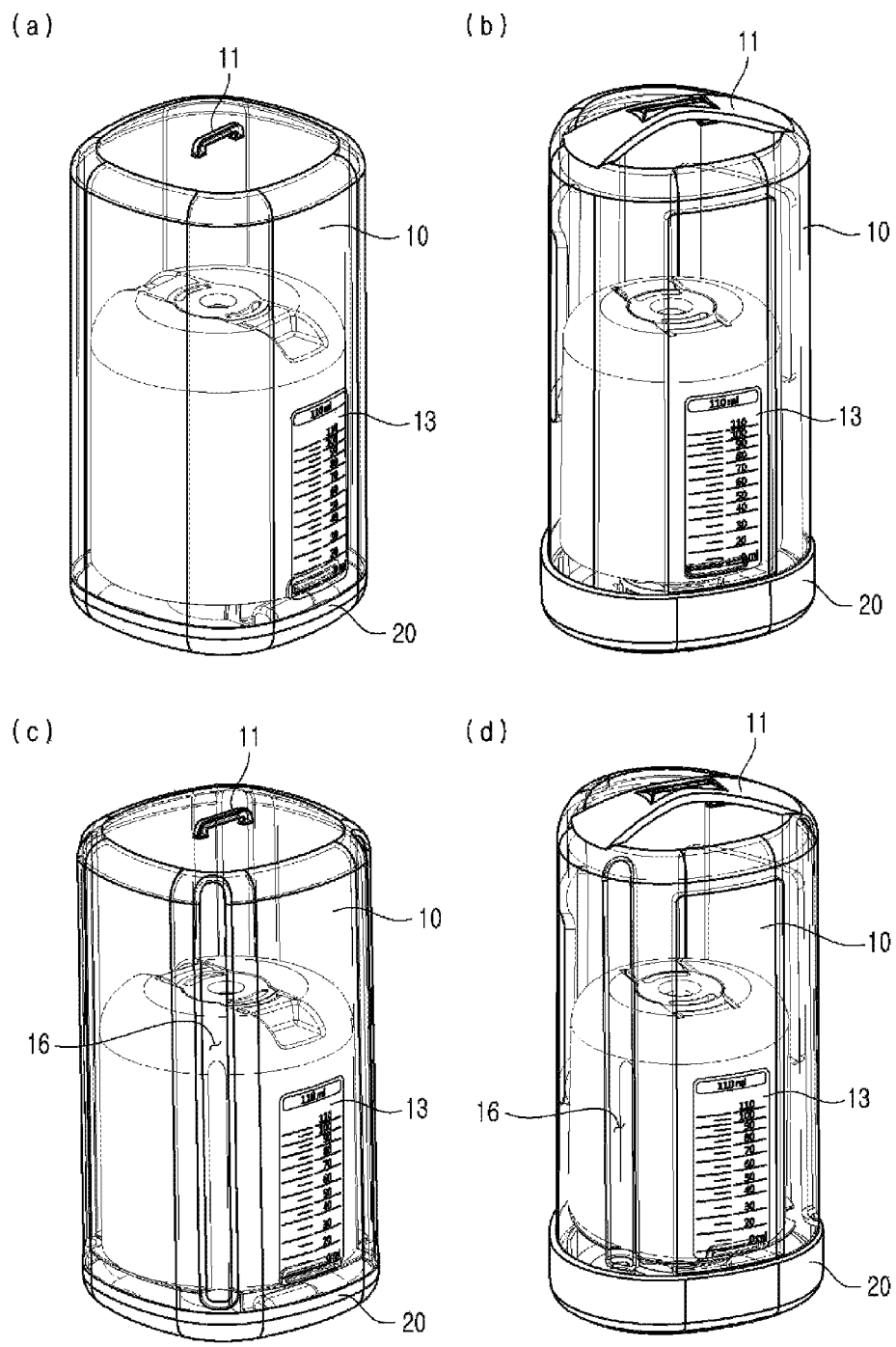
FIG. 1 illustrates perspective views of embodiments of a balloon infuser according to the present invention.

FIGS. 1A and 1C illustrate shapes that are close to a rectangular column and FIGS. 1B and 1D illustrate shapes that are close to a triangular column. Although not illustrated, the balloon infuser may have a shape that is close to a polygonal column other than a rectangular or triangular column, or may have a circular column shape.

FIGS. 1C and 1D illustrate a grip groove 16 in a vertical direction formed such that the user may easily grip the balloon infuser to improve a structural stability.

Figure 2:
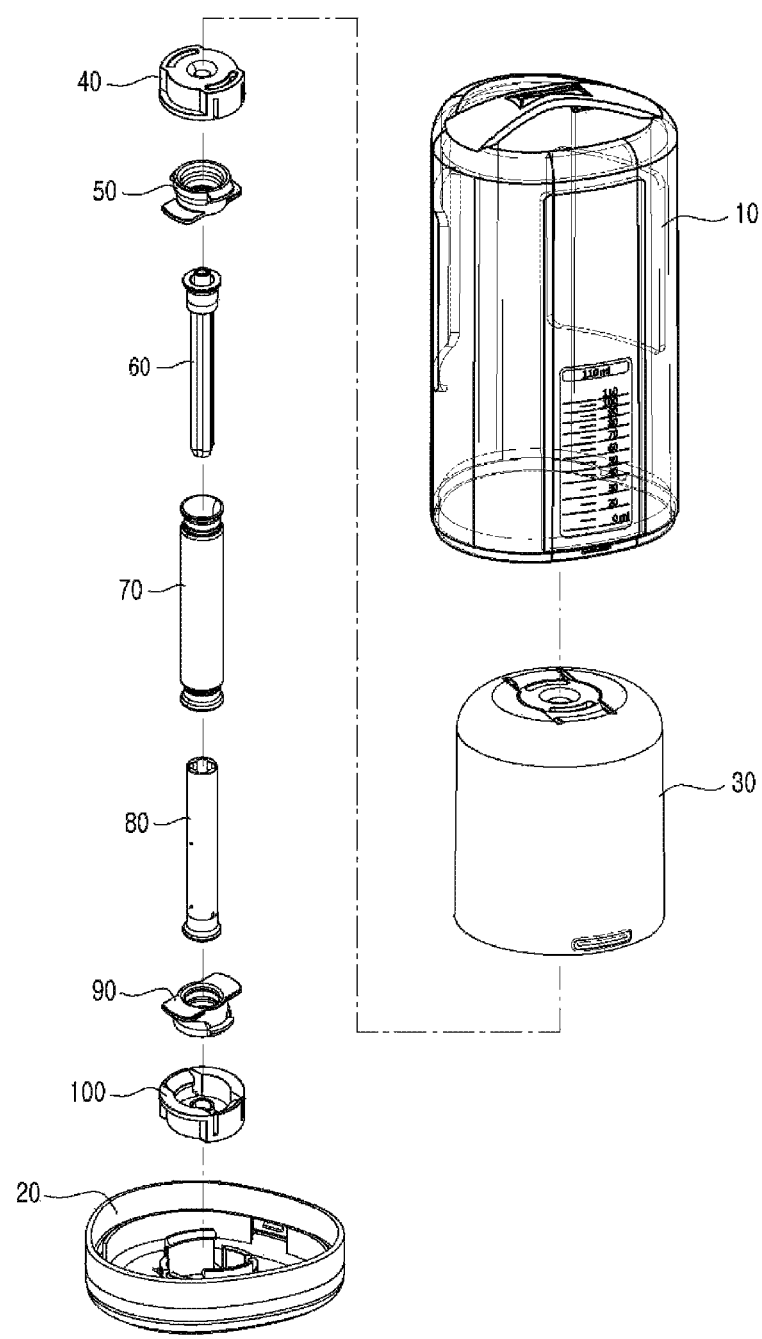
FIG. 2 is an exploded perspective view of the balloon infuser according to the present invention.

FIG. 2 is an exploded perspective view of the balloon infuser according to the present invention. Although FIG. 1A is illustrated as an example, the internal components will be the same except that the shapes of the upper cover 10 and the lower cover 20 are different from those of FIG. 1A.

The balloon infuser according to the present invention includes an upper cover 10, an elevation part 30, an upper connector holder 40, an upper connector 50, an inner shaft 60, an expansion member 70, an outer shaft 80, a lower connector 90, and a lower connector holder 100, and a lower cover 20 is located on the lowermost side.

The upper connector 50 and the lower connector 90 may be formed of the same member, and the upper connector holder 40 and the lower connector holder 100 also may be formed of the same member. Through this, the balloon infuser may be easily manufactured and manufacturing costs may be lowered.

The upper cover 10 and the lower cover 20 form an external appearance of the balloon infuser according to the present invention. A scale mark 13 is printed in the upper cover 10, and an accurate amount of contents may be guided because a scale mark 13 is indicated by elevating the scale indication line 34 of the elevation part 30 as the elevation part 30 is elevated.

The upper connector holder 40 and the upper connector 50 are coupled to the elevation part 30. The upper connector holder 40 and the upper connector 50 are firmly fixed through snap coupling without using an adhesive.

The lower connector holder 100 and the lower connector 90 are fixed even to a lower opening 21 of the lower cover 20 through snap coupling without using an adhesive.

An inner shaft 60, an outer shaft 80, and an expansion member 70 are located between the upper connector 50 and the lower connector 90.

The inner shaft 60 is fixed to the lower cover 30 by the upper connector 50.

The outer shaft 80 is fixed to the elevation part 20 by the lower connector 90.

As contents is infused into the balloon infuser, the expansion member 70 is expanded and the inner shaft 60 and the elevation part 30 coupled thereto are lifted (FIG. 3C). In contrast, as contents is discharged from the balloon infuser, the expansion member 70 is contracted and the inner shaft 60 and the elevation part 30 coupled thereto are lowered (FIG. 3A).

Hereinafter, the configurations will be described in detail.

2. DETAILED DESCRIPTION OF ELEMENTS

The upper cover 10, the lower cover 20, the elevation part 30, the upper connector holder 40, the upper connector 50, the inner shaft 60, the expansion member 70, and the outer shaft 80 will be sequentially described with reference to FIGS. 7 to 14.

Figure 7:
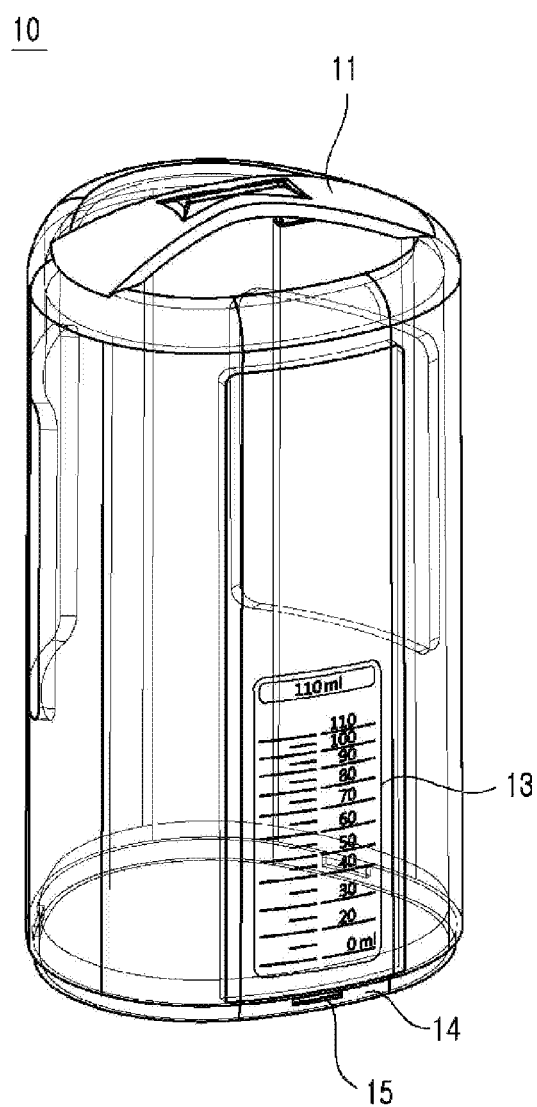
FIG. 7 illustrates perspective views of an upper cover 10 of the balloon infuser according to the present invention.

FIG. 7 illustrates the upper cover 10.

The upper cover 10 is formed of a transparent or translucent material such that the user may view the elevation part 30. Through this, the user may recognize which scale of the scale marks 13 the elevation part 30 that elevates inside the upper cover indicates.

A holder part 11 is located on an upper surface of the upper cover 10, and the balloon infuser is held on a separate holder to allow the user to conveniently use the balloon infuser.

The scale marks 13 are printed on one surface of one side of the upper cover 10. The scale marks 13 indicate capacities of contents along a vertical direction, and the intervals between the scale marks on the lower side may be larger than the intervals between the scale marks on the upper side. The number of the scale marks 13 indicated by the scale indication line 34 of the elevation part 30 refers to a capacity of contents.

For coupling of the upper cover 10 and the lower cover 20, the stepped portion 14 is located along an outer periphery of a distal end of the upper cover 10. During coupling, a stepped portion 24 of the lower cover 20 is located at the stepped portion 14 of the upper cover 10.

A coupling recess 15 is located at a portion of the stepped portion 14. A coupling boss 25 of the lower cover 10 is inserted into and firmly fixed to the coupling recess 15.

Although it is illustrated in the embodiment of FIG. 7 that three coupling recesses 15 are provided because the upper cover 10 has a shape that is close to a triangular column, four coupling recesses 15 will be provided when the upper cover has a shape that is close to a rectangular column as in FIGS. 1A and 1C and another plurality of coupling recesses will be provided in the case of a polygonal column. It is preferable that coupling recesses be located at two or more locations along an outer periphery of the upper cover for coupling in the case of a circular column shape.

Figure 8:
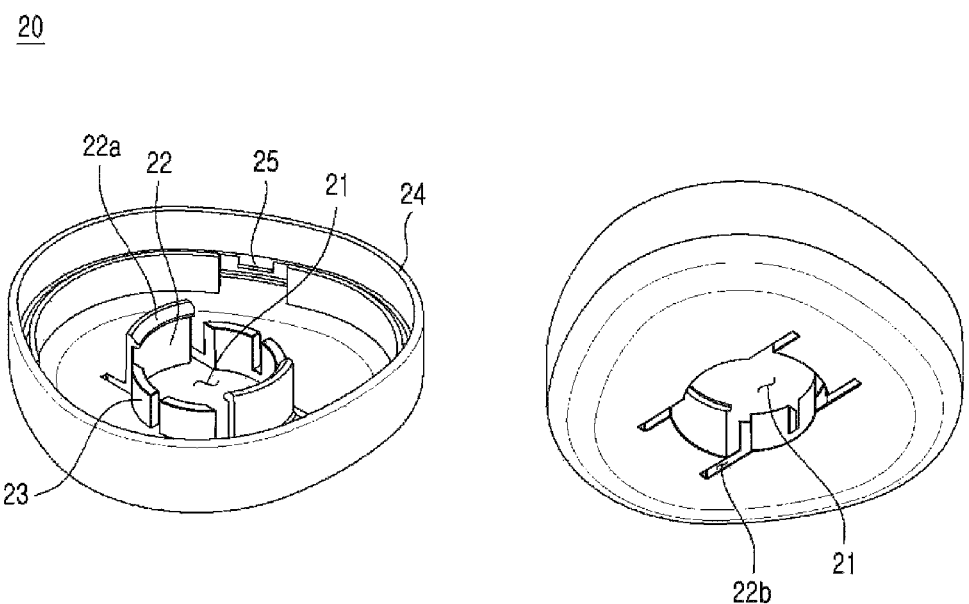
FIG. 8 illustrates perspective views of a lower cover 20 of the balloon infuser according to the present invention. For description, a top perspective view and a bottom perspective view are illustrated together.

FIG. 8 illustrates the lower cover 20.

A lower opening 21 is located on a central inner side of the lower cover 20. The user may approach an infusion opening 81 through the lower opening 21, and may infuse contents through the lower opening 21 or supply a quantity of contents to the user.

A lower connector holder stopping step 22 and a lower connector holder support 23 protrude upwards in a radial direction along a border of the lower opening 21. One lower connector holder stopping step 22 and one lower connector holder support 23 are located to face each other, the locations and numbers thereof may be changed.

A lower connector holder seating part 22a protruding inwards is located at a distal end of an upper surface of the lower connector holder stopping step 22.

An inclined surface to an inner lower side is located on an inner surface of the lower connector holder seating part 22a. An outward step is formed on a distal end surface of a lower side of the inclination surface, and when the lower connector holder 100 is inserted, the stopping step of the lower connector holder 100 is moved along the inclined surface and then is snap-coupled inwards. Accordingly, movement to an upper side of the lower connector holder 100 is restricted.

Meanwhile, for the coupling, slight leftward/rightward movement of the lower connector holder stopping step 22 and the lower connector holder seating part 22a are necessary and thus a seating part spacing space 22b is located outside.

Figure 5:
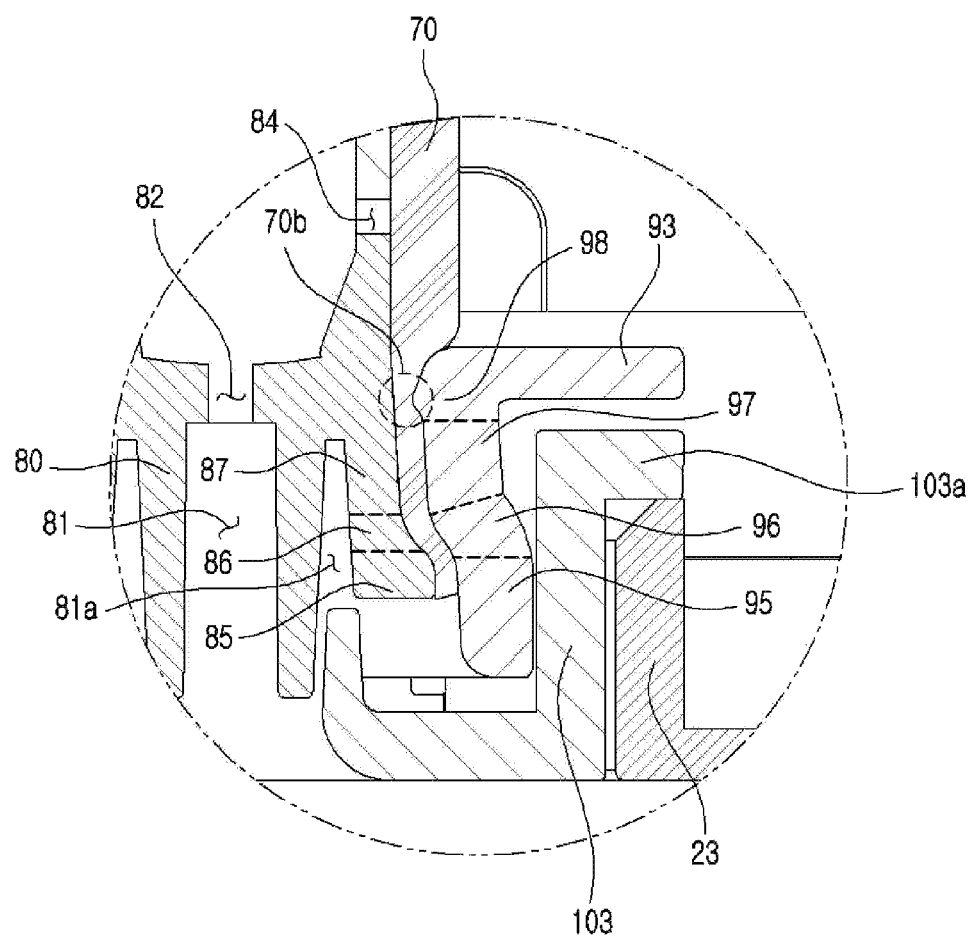
FIG. 5 is an enlarged sectional view of part "B" of FIG. 3A, and is a sectional view viewed from direction A-A of FIG. 10 as in FIG. 4.

The lower connector holder support 23 is located at the lower connector holder stopping step 22 at an angle of 90 degrees. When the lower connector holder 100 is into the lower opening 21, as illustrated in FIG. 5, a lower cover seating part 103a is located above the lower connector holder support 23. Accordingly, movement to a lower side of the lower connector holder 100 is restricted.

Through the snap coupling, the upward and downward movements of the lower connector holder 100 with respect to the lower cover 20 are restricted by the lower connector holder stopping step 22 and the lower connector holder support 23, respectively so that the lower connector holder 100 may be firmly fixed without using an additional member such as an adhesive.

Figure 9:
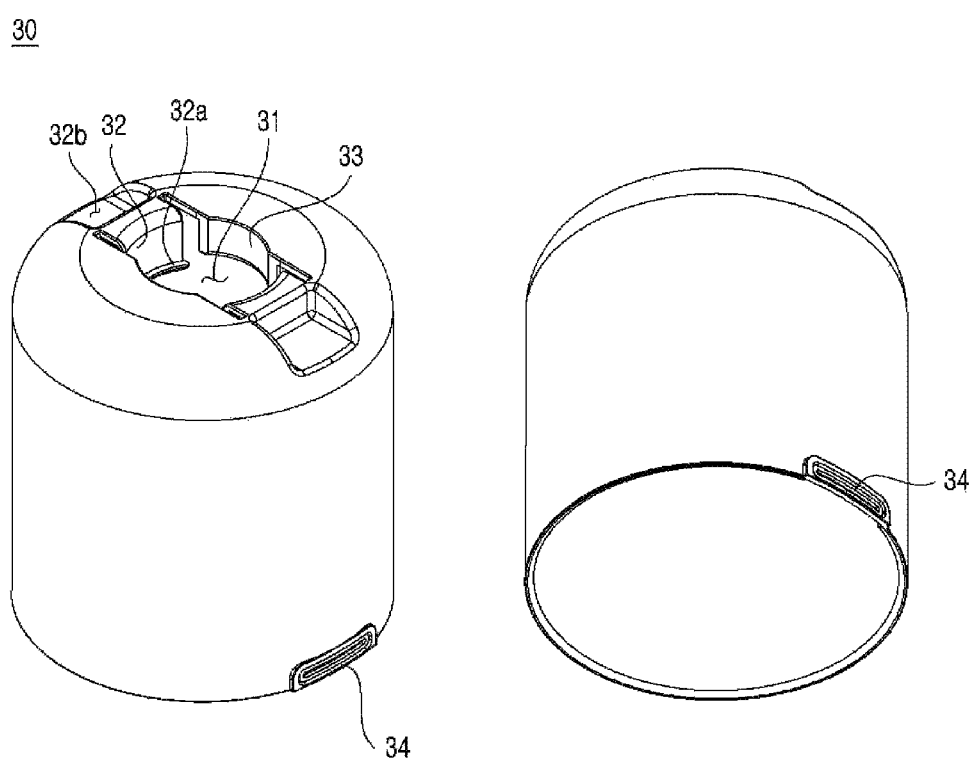
FIG. 9 is an exploded perspective view of an elevation part 30 of the balloon infuser according to the present invention. For description, a top perspective view and a bottom perspective view are illustrated together.

FIG. 9 illustrates the elevation part 30.

The inner shaft 60 is elevated with respect to the outer shaft 80 fixed to the lower cover 20 according to the amount of the contents, and the elevation part 30 fixed to the inner shaft 60 is elevated by the upper connector holder 40 and the upper connector 50.

That is, the elevation part 30 is elevated in correspondence to the amount of the contents, and accordingly, the scale indication line 34 may indicate the amount of the contents corresponds to which degree on the scale mark 13.

The scale indication line 34 is located on one side of a distal end of the elevation part 30. Because the scale indication line is linear, the amount of the contents printed on the scale mark which is also linear may be accurately indicated.

For this function, the elevation part 30 has to be firmly fixed to the upper shaft 60, and to achieve this, an upper connector holder stopping step 32 and an upper connector holder support 33 are located radially in an upper elevation part opening 31 located at an upper portion of the elevation part 30 along a border thereof so that the elevation part 30, the upper connector holder 40, the upper connector 50, and the upper shaft 60 are firmly fixed without using an adhesive.

The structures of the upper elevation part opening 31, the upper connector holder stopping step 32, and the upper connector holder support 33 are the same as those of the lower opening 21, the upper connector holder stopping step 22, and the lower connector holder support 23, and only the installation directions thereof are 180 degrees opposite to each other (that is, opposite upward and downward directions). Through this, because the connector holders and the connectors that are the same components may be used for the upper and lower sides, manufacturing costs may be lowered and convenience of manufacturing may be achieved.

Meanwhile, the seating part spacing space 22b of the lower cover 20 is recessed to protrude to one side (a shape that protrudes upwards in FIG. 8), whereas the seating part spacing space 32b of the elevation part 30 is recessed outwards.

An upper connector holder seating part 32b protruding inwards is located at a distal end of a lower side of the upper connector holder stopping step 32. Accordingly, when the upper connector holder 40 is coupled to the upper elevation part opening 31 downwards, the upper connector stopping step 42 of the upper connector holder 42 is seated on the upper side of the upper connector holder seating part 32a so that the upper connector 40 may be prevented from moving downwards independently from the elevation part 30.

Meanwhile, when the upper connector holder 40 is coupled to the upper elevation part opening 31 downwards, the elevation part support 43 is located at a lower end of the upper connector holder support 33. Accordingly, the upper connector 40 may be prevented from moving independently from the elevation part 30.

Through the structure, both the upward movement and the downward movement of the upper connector holder 40 with respect to the elevation part 30 are restricted, the upper connector holder 40 may be firmly fixed without using an additional member such as an adhesive and the elevation part 30 and the upper connector 40 are elevated together.

FIG. 10 illustrates the upper connector holder 40. The lower connector holder 100 has the same structure as the upper connector holder 40, and as illustrated in FIG. 2, they are installed in opposite directions when the balloon infuser is manufactured.

The upper connector holder 40 is inserted into the upper elevation part opening 31 of the elevation part 30.

An upper connector holder opening 41 is located at the center of the upper connector holder 40.

The upper connector stopping step 42 and the elevation part support 43 are located radially along an outer surface of the upper connector holder 40. It is preferable that a pair of upper connector stopping steps 42 and a pair of elevation party supports 43 be located to be opposite to each other.

Figure 6:
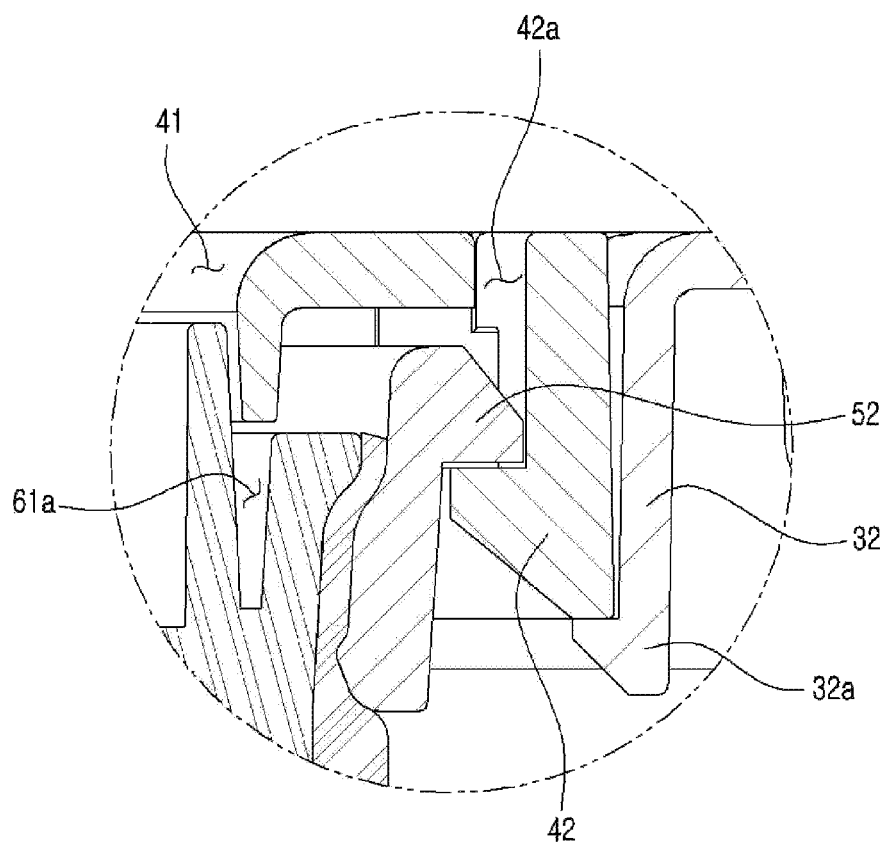
FIG. 6 is an enlarged sectional view of a part that is radially shifted by 90 degrees from part "A" of FIG. 3A, and is a sectional view viewed from direction C-C when

Although the outer surface of the upper connector stopping step 42 is vertical, an inclined surface that protrudes inwards and is inclined such that a radius thereof becomes smaller as it goes from the upper side to the lower side is located on an inner surface of the upper connector stopping step 42. An upper distal end surface of the inclined surface is stepped outwards, and as illustrated in FIG. 6, the upper connector holder coupling part 52 of the upper connector 50 may be inserted into the step. That is, when the upper connector 50 is inserted toward the upper connector holder 40 from the lower side to the upper side, the upper connector holder coupling part 52 is snap-coupled inwards while moving along the inclined surface of the upper connector stopping step 42. Accordingly, the upper connector 50 may be prevented from moving downwards independently from the upper connector holder 40.

Meanwhile, for the coupling, because the upper connector stopping step 42 has to move slightly leftwards and rightwards when the upper connector 50 is coupled, the seating part spacing space 42*a* is located inside the upper connector stopping step 42.

An elevation part seating part 43*a* protruding outwards is located at a distal end of the lower side of the elevation part support 43.

The elevation part support 43 not only prevents the upper connector holder 40 from moving upwards independently from the elevation part 30 as described above but also prevents the upper connector 50 from moving upwards independently from the upper connector holder 40.

Figure 4:
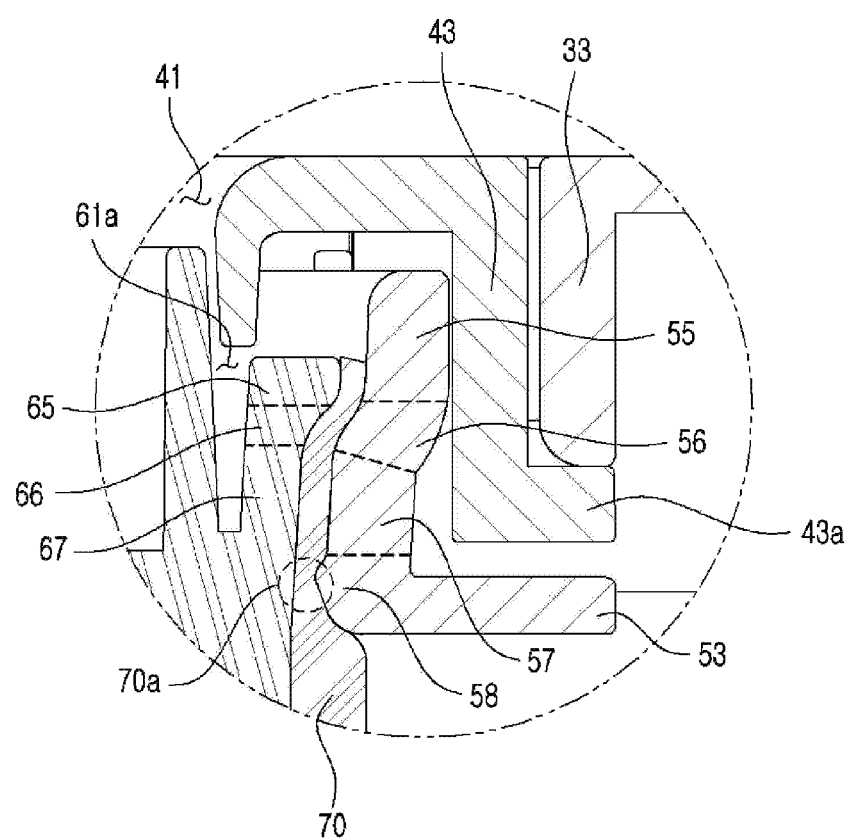
FIG. 4 is an enlarged sectional view of part "A" of FIG. 3A, and is a sectional view viewed from direction A-A when

That is, as illustrated in FIG. 4, the elevation seating part 43*a* is located on the upper side of an upper connector shoulder 53 of the upper connector 50 to prevent the upper connector 50 from moving upwards independently from the upper connector holder 40 while the elevation part seating part 43*a* contacts a lower end of the upper connector holder support 33 to prevent the upper connector holder 40 from moving upwards independently form the elevation part 30.

FIG. 11 illustrates the upper connector 50. As described above, the lower connector 90 has the same structure as the upper connector 50. Meanwhile, as illustrated in FIG. 2, the installation directions of the lower connector 90 and the upper connector 50 are opposite to each other when the balloon infuser is manufactured.

The upper connector 50 is inserted into a lower side of the upper connector holder 40, an upper connector opening 51 is located at an upper central portion of the upper connector, and an inner shaft 60 is inserted into the upper connector opening 51.

As illustrated in FIG. 4, an outer periphery that forms the upper connector opening 51 may be classified into a first upper outer wall body 55, a second upper outer wall body 56, and a third upper outer wall body 57, and a protrusion 58 is located at the outer periphery. The configurations will be described in detail together with the coupling structure.

An upper connector holder coupling part 52 is located on the upper side of an outer periphery of the upper connector 50. Because the upper side of the upper connector holder coupling part 52 is inclined upwards, the upper connector stopping step 42 may be moved more easily while the inclined surface of the upper connector stopping step 42 meets the upper connector holder coupling part 52.

As described in FIG. 6, when the upper connector 50 is inserted toward the upper connector holder 40 from the lower side to the upper side, the upper connector holder coupling part 52 is snap-coupled inwards while moving along the inclined surface of the upper connector stopping step 42. The upper connector 50 may be prevented from moving downwards independently from the upper connector holder 40.

An upper connector shoulder 53 protruding outwards by a specific distance is located on the lower side of an outer peripheral surface of the upper connector 50. As illustrated in FIG. 4, the upper connector shoulder 53 is located on the lower side of the elevation part support 43*a* to prevent the upper connector 50 from moving upwards independently from the upper connector holder 40.

FIG. 12 illustrates the inner shaft 60.

The lower side of the inner shaft 60 is firmly fixed to the elevation part 30 by the upper connector 50 and the upper connector holder 40. The inner shaft 60 is a component that elevates the elevation part 30 while elevating according to the amount of contents.

A flexible expandable member 70 is firmly fixed between an upper side of the inner shaft 60 and the upper connector 50.

The body 69 at a middle lower portion of the inner shaft 60 is guided to be slid in a space in the outer shaft 80. To achieve this, it is preferable that the shape of the body 69 correspond to the shape of a hollow part 88 of the outer shaft 80, and in particular, it is preferable that one or more protrusions be located for smooth guide. Although FIGS. 12 and 14 illustrate four protrusions and hollow parts 88 corresponding thereto, but the numbers and shapes thereof may be arbitrary.

A first upper inner wall body 65, a second upper inner wall body 66, and a third upper inner wall body 67 are located at an upper portion of the inner shaft 60. Through the forms and configurations of the inner wall bodies 65, 66, and 67, ascending or descending of the inner shaft 60 with respect to the elevation part 30 is restricted so that the inner shaft 60 may be firmly fixed. The configurations will be described in detail together with the coupling structure.

A cylindrical hollow body 61 is located at an upper central portion of the inner shaft 60, and the cylindrical hollow body 61 passes through the upper connector opening 51 and the upper connector holder opening 41 and reaches the upper elevation part opening 31.

A inner wall body spacing space 61*a* is located between an radially outer side of the cylindrical hollow body 61 and the first upper inner wall body 65.

If the contents are infused into the balloon infuser, the expandable member 70, which will be described below, is expanded and the inner shaft 60 is lifted from the outer shaft 80 by the pressure.

Accordingly, the elevation part 30 fixed to the inner shaft 60 by the upper connector 50 and the upper connector holder 40 is lifted, and due to the lifting of the elevation part 30, the scale indication line 34 is lifted to indicate the scale mark 13.

FIG. 13 illustrates the expandable member 70.

The shape of the expandable member 70 illustrated in FIG. 13 has a shape in a state in which contents are not infused (FIG. 3A), and if the contents are infused, the flexible expandable member 70 is expanded (FIGS. 3B and 3C).

As illustrated in FIGS. 3B and 3C, because the upper side and the lower side of the expandable member 70 are fixed by the inner shaft 60 and the outer shaft 80, a central portion of the expandable member 70 is expanded or contracted.

It is sufficient as long as the expandable member 70 is flexible, the expanding and contracting forces may become excellent and the sanitary performance may be increased by using silicon in an embodiment.

In particular, although it will be described below in the description of the following coupling structure, the expandable member 70 is located between the upper connector 50 and the inner shaft 60 such that the upper connector 50 and the inner shaft 60 are sealed without using an adhesive, and likewise, the expandable member 70 is located between the lower connector 90 and the outer shaft 80 such that the lower connector 90 and the outer shaft 80 are coupled to be sealed without using an adhesive.

FIG. 14 illustrates the outer shaft 80.

The lower side of the outer shaft 80 is fixed by the lower connector 90 and the lower connector holder 100, and in particular, may be firmly fixed by the lower cover 20 regardless of the amount of the contents.

A flexible expandable member 70 is fixed between a lower side of the outer shaft 80 and the lower connector 90.

As described above, the hollow part 88 of the outer shaft 80 guide the inner shaft 60 such that the inner shaft 60 may be elevated. To achieve this, the shape of the hollow part 88 corresponds to the shape of the body 69 of the inner shaft 60.

An infusion opening 81 is located at a lower central portion of the outer shaft 80. If the contents are infused through the infusion opening 81, they pass through the infusion opening 82 of a smaller diameter and reach the hollow part 88 (see FIGS. 3A to 3C and 5).

A pair of upper holes 83 and a pair of lower infusion holes 84 are located on an outer surface of the hollow part 88. Through the upper infusion holes 83 and the lower infusion holes 84, the contents inside the hollow part 88 are infused into the expandable member 70 and expand the expandable member 70.

The upper infusion hole 83 is located at a central portion of the hollow part 88 and the lower infusion hole 84 is located close to a distal end of a lower side of the hollow part 88 to decrease a dead space, which will be described below.

A first lower inner wall body 85, a second lower inner wall body 86, and a third lower inner wall body 87 are located at a lower portion of the outer shaft 80. Through the forms and configurations of the inner wall bodies 85, 86, and 87, ascending or descending of the outer shaft 80 with respect to the lower cover 20 is restricted so that the inner shaft 60 may be firmly fixed. The configurations will be described in detail together with the coupling structure.

A inner wall body spacing space 81a is located between an radially outer side of the infusion opening 81 and the first lower inner wall body 85.

3. FIRM COUPLING STRUCTURE WITHOUT ADHESIVE

It is preferable that the adhesive be minimally used due to the characteristics of the medical instrument. However, as described in the prior art, it is not easy to exclude an adhesive while maintaining the sealing state of the contents in the medical instrument, such as a balloon infuser, which has a complex structure. The present inventors solved the problem through a structure, which will be described below.

During the manufacturing process, after an upper end portion and a lower end portion of the expandable member 70 surrounding the inner shaft 60 and the outer shaft 80 are pushed into the upper connector 50 and the lower connector 90, the upper connector holder 40 and the lower connector holder 100 are seated on the upper connector 50 and the lower connector 90. Through the method, internal components are coupled without using a separate adhesive.

Meanwhile, although a snap-coupling method will be described for convenience of manufacturing, it is also mentioned that a nut method, for example, using a thread is possible without using an adhesive.

The connection strictures will be described with reference to FIGS. 4 to 6.

FIG. 4 is an enlarged sectional view of part "A" of FIG. 3A, and is a sectional view viewed from direction A-A when FIG. 10 is referenced.

FIG. 5 is an enlarged sectional view of part "B" of FIG. 3A. Like FIG. 4, FIG. 5 is a sectional view viewed from A-A of FIG. 10. Although the coupling structure of the lower connector 90 is substantially the same as the coupling structure of the upper connector 50, unique elements of the outer connector 80 is additionally illustrated.

FIG. 6 is an enlarged sectional view of a part that is radially shifted by 90 degrees from part "A" of FIG. 3A, and is a sectional view viewed from direction C-C when FIG. 10 is referenced. It is noted that FIGS. 3A to 3C also are sectional perspective views viewed from C-C when FIG. 10 is referenced.

A coupling structure of the upper connector 50 of FIG. 4 will be described.

The inner shaft 60, the expandable 70, the upper connector 50, the upper connector holder 40, and the elevation part 30 are coupled from the center to the outside. Both the upward movement and the downward movement thereof with respect to each other are restricted without using a separate adhesive.

The flexible expandable member 70 covers the inner shaft 60 by a height substantially from an outside of the inner shaft 60 to an upper portion of the inner shaft. The upper connector 50 is located on the outside of the expandable member 70 to a height that is higher than the expandable member 70.

As classified by a dotted line of FIG. 4, the inner wall of the inner shaft 60 may be classified into the first upper inner wall body 65, the second upper inner wall body 66, and the third upper inner wall body 67. As compared with the first upper inner wall body 65 and the third upper inner wall body 67, the second upper inner wall body 66 has a shape that is inclined inwards further.

The shape also may be identified in the upper connector 50 outside the expandable member 70, the inclinations of the inner surfaces of the first upper outer wall body 55, the second upper outer wall body 56, and the third upper outer wall body 57 are substantially similar to the inclinations of the outer surfaces of the first upper inner wall body 65, the second upper inner wall body 66, and the third upper inner wall body 67.

In this way, because the inclinations of the inner wall bodies 65, 66, and 67 and the outer wall bodies 55, 56, and 57 are made to be similar and then the flexible expandable member 70 is inserted between them, the expandable member 70 functions as an O-ring, helping seal the contents and firmly fixing the inner wall bodies 65, 66, and 67 and the outer wall bodies 55, 56, and 57 by using frictional forces.

A protrusion 58 is located below the third upper outer wall body 57. The height of the protrusion 58 is smaller than the thickness of the expandable member 70. Although the inner wall bodies 65, 66, and 67 are located at locations corresponding to the outer wall bodies 55, 56, and 57, there is no corresponding shape at a location of the inner shaft 60 corresponding to the protrusion 58.

That is, as indicated by "70a", the protrusion 58 fixes the expandable member 70 while pressing the flexible expandable member 70.

Meanwhile, the upper connector 50 and the upper connector holder 40 also are firmly fixed to the elevation part 30. As illustrated in FIGS. 10 and 11, a pair of upper connectors 50 and a pair of upper connector holders 40, which are different structures, are provided, and are fixed through interactions.

As illustrated in FIG. 4, with reference direction A-A of FIG. 10, the upward movement of the upper connector 50 is restricted because the upper connector shoulder 53 is stopped by the elevation part seating part 43a of the upper connector holder 40, the upward movement of the upper connector holder 40 is restricted because the elevation part seating part 43a is stopped by the upper connector holder support 33 of the elevation part 30.

As illustrated in FIG. 6, with reference direction C-C of FIG. 10, the downward movement of the upper connector 50 is restricted because the upper connector holder coupling part 50 is stopped by the upper connector stopping step 42 of the upper connector holder 40, the downward movement of the upper connector holder 40 is restricted because the upper connector stopping step 42 is stopped by the upper connector holder seating part 32a.

Through the method, both the upward and downward movements of the upper connector holder 40 are restricted, and the upper connector 50, the upper connector holder 40, and the elevation part 30 are firmly fixed without using an adhesive.

Meanwhile, in spite of the firm fixing, the present invention may allow the manufacturer to easily assemble components.

As illustrated in FIG. 4, it is easy to insert the upper connector 50 from a lower side to an upper side of the upper connector holder 40. Further, it is also easy to insert the upper connector holder 40 from a lower side to an upper side of the elevation part 30.

As illustrated in FIG. 6, when the upper connector 50 is inserted from a lower side of the upper connector holder 40, the inclined surface of the upper connector holder coupling part 52 contacts the inclined surface of the upper connector stopping step 42. If the manufacturer applies a force further, the upper connector holder stopping step 52 is snap-coupled over the upper connector stopping step 42 while the upper connector stopping step 42 pushed by the upper connector holder stopping step 52 is widened outwards by using the stopping step spacing space 42a.

Further, when the upper connector holder 40 is inserted from a lower side of the elevation part 30, it contacts the inclined surface of the upper connector holder seating part 32a of the upper connector stopping step 42. If the manufacturer applies a force further, the upper connector holder stopping step 52 is snap-coupled over the upper connector holder seating part 32a while the upper connector holder seating part 32a pushed by the upper connector stopping step 42 is widened outwards by using the seating part spacing space 32b.

Meanwhile, the coupling relationship and the advantages due to the coupling relationship may be still applied to the outer shaft 80, the expandable member 70, the lower connector 90, the lower connector holder 100, and the lower cover 20. FIG. 5 illustrates the structure.

The inner wall of the outer shaft 80 may be classified into a first lower inner wall body 85, a second lower inner wall body 86, and a third lower inner wall body 87, and the second lower inner wall body 86 is inclined inwards. The shape may be identified not only in the lower connector 90 but also in the first lower outer wall body 95, the second lower outer wall body 96, and the third lower outer wall body 97. The firm fixing may be made through the combination. A protrusion 98 is located below the third lower outer wall body 97 to press the flexible expandable member 70 as indicated by "70b".

Further, the downward movement of the lower connector 90 is restricted because the lower connector shoulder 93 is stopped by the lower cover seating part 103a of the lower connector holder 100, and the upward movement of the upper connector holder 100 is restricted because the lower cover seating part 103a is stopped by the lower connector holder support 103 of the lower cover 100.

In direction C-C of FIG. 10, the restriction of the downward movements of the lower connector 90 and the lower connector holder 100 also uses the same principle.

Through the method, both the upward and downward movements of the lower connector 90 and the lower connector holder 100 are restricted such that the lower connector 90 and the lower connector holder 100 may be firmly fixed.

Through the above-mentioned methods, the manufacturer may easily manufacture the balloon infuser, and once the balloon infuser is completed, it may be firmly fixed and cannot be disassembled even though a separate adhesive is not used.

4. DEAD SPACE REDUCING EFFECTS

As illustrated in FIGS. 3B and 3C, the upper infusion hole 83 is located at a central portion of the hollow part 88 and the lower infusion hole 84 is located close to a distal end of the lower side of the hollow part 88. In this way, the infusion holes 83 and 84 are provided to reduce a dead space.

The amount of the contents inside the expandable member 70 gradually decreases as the contents inside the expandable member 70 is supplied while being discharged to the outside.

Accordingly, the discharge of the contents is assisted due to a maximum contraction force on a transverse central line of the expandable member 70 because the upper infusion hole 83 is located at the center of the hollow part 88, and the discharge of the contents that are deposited as a transverse contraction force of the expandable member 70 is not applied is assisted because the lower infusion hole 84 is located at a distal end of the lower side of the hollow part 88.

5. DESCRIPTION OF OTHER EMBODIMENTS

Another example of the present invention will be described with reference to FIG. 15.

According to the embodiment of FIG. 15, as compared with the above-described embodiment, the coupling method of the upper connector holder 40 and the elevation part 30 and the coupling method of the lower connector holder 100 and the lower cover 20 are different. In the drawings, different parts are denoted by separate reference numerals.

A pair of lower connector holder supports 23 of the lower cover 20 are present in the above-described embodiment, a lower connector holder insertion part 23' is located instead of the lower connector holder support 23 and a lower connector holder insertion recess 23a' is located at a central portion of the lower connector holder insertion part 23' in the embodiment of FIG. 15.

A lower cover insertion boss 103a' is provided at a central portion of the lower cover seating part 103a of the lower connector 100, and is inserted into and firmly coupled to a lower connector holder insertion recess 23a'.

Like the upper connector holder 40 and the elevation part 30, an elevation part insertion boss 43a' is located on the elevation part seating part 43a of the upper connector holder 40 and is inserted into the upper connector holder insertion recess of the elevation part (not illustrated).

Through the structure, a harder coupling structure may be formed as compared with the above-mentioned embodiments.

Although the preferred embodiments of the present invention have been described, it will be understood by those skilled in the art that the present invention can be variously corrected and modified without departing from the spirit and scope of the present invention claimed in the claims.

The invention claimed is:

1. A balloon infuser comprising:
an upper cover (10) in which a scale mark (13) including linear scales is displayed;
a lower cover (20) fixed to a lower side of the upper cover (10);
a flexible expandable member (70) located inside the upper cover (10) and in which contents are accommodated;
an elevation part (30) elevated according to an expansion degree of the expandable member (70) and having a scale indication line (34) on one surface thereof, the scale indication line (34) indicating the scale mark (13);
an upper connector holder (40) coupled to an upper elevation part opening (31) located on an upper side of the elevation part (30);
an upper connector (50) coupled to the upper connector holder (40);
an inner shaft (60) coupled to the upper connector (50);
a lower connector holder (100) coupled to a lower opening (21) of the lower cover (20);
a lower connector (90) coupled to the lower connector holder (100); and
an outer shaft (80) coupled to the lower connector (90);
wherein the expandable member (70) covers the inner shaft (60) such that the inner shaft (60) is sealed, and
wherein a hollow part (88) is located in the outer shaft (80), and the inner shaft (60) is inserted into the hollow part (88) to be elevated through a slide movement.

2. The balloon infuser of claim 1, wherein an infusion opening (81) communicating with the lower opening (21) is located at a central portion of the outer shaft (80),
wherein the infusion opening (81) communicates with the hollow part (88) through an infusion hole (82),
wherein a plurality of infusion holes (83, 84) are located in the hollow part (88),
wherein the plurality of infusion holes (83, 83) are seated from the outside by the expandable member (70), and
wherein if contents are infused through the infusion opening (81), the infused contents are introduced into the hollow part (88) through the infusion hole (82) and are discharged into the expandable member (70) through the plurality of infusion holes (83, 84) to expand the expandable member (70) and lifting the inner shaft (60).

3. The balloon infuser of claim 2, wherein the plurality of infusion holes (83, 84) include:
a pair of upper infusion holes (83) located at a central portion of the hollow part (88); and
a pair of lower infusion holes (84) located below the hollow part (88).

4. The balloon infuser of claim 3, wherein the height of the upper infusion hole (83) corresponds to the central height of the expansion member (70) in a maximally expanded state.

5. The balloon infuser of claim 1, wherein the upper elevation part opening (31) and the lower opening (21) have the same shape and are formed in 180 degree opposite directions,
wherein the upper connector holder (40) coupled to the upper elevation part opening (31) and the lower connector holder (100) coupled to the lower opening (21) are the same component, and
wherein the upper connector (50) and the lower connector (90) are the same components.

6. The balloon infuser of claim 5, wherein the upper connector holder (40) is snap-coupled in the upper elevation part opening (31) without using an adhesive, the upper connector holder (40) and the upper connector (50) are snap-coupled to each other without using an adhesive, and the expandable member (70) is located between the upper connector (50) and the inner shaft (60) to be sealed without using an adhesive, and
wherein the lower connector holder (100) is snap-coupled in the lower opening (21) without using an adhesive, the lower connector holder (100) and the lower connector (90) are snap-coupled to each other without using an adhesive, and the expandable member (70) is located between the lower connector (90) and the outer shaft (80) to be sealed without using an adhesive.

7. The balloon infuser of claim 6, wherein an upper side of the inner shaft (60) is coupled to the upper connector (50),
wherein the shapes of inner wall bodies (65, 66, 67) of the inner shaft (60) correspond to the shapes of outer wall bodies (55, 56, 57) of the upper connector (50), and
wherein the expandable member (70) is located between the inner wall bodies (65, 66, 67) and the outer wall bodies (55, 56, 57).

8. The balloon infuser of claim 7, wherein any one inner wall body (66) of the inner wall bodies (65, 66, 67) and any one outer wall body (56) corresponding to the any one inner wall body (66) are inclined with respect to the other inner wall bodies (65, 67) and the other wall bodies (55, 57), and
wherein a protrusion (58) protruding inwards is located on another outer wall body (57) of the outer wall bodies (55, 56, 57), and the protrusion (58) presses the expandable member (70).

9. The balloon infuser of claim 1, wherein a pair of upper connector holder stopping steps (32) and a pair of upper connector holder supports (33) are radially located along a border of the upper elevation part opening (31), and an upper connector stopping step (42) and an elevation part support (43) are located radially along an outer periphery of the upper connector holder (40), and
wherein an upper connector holder seating part (32a) protruding inwards is located at a distal end of a lower side of the upper connector holder stopping step (32), and an elevation part seating part (43a) protruding outwards is located at a distal end of a lower side of the elevation part support (43).

10. The balloon infuser of claim 9, wherein a downward movement of the upper connector holder (40) is restricted by locating the upper connector holder seating part (32a) below the upper connector stopping step (42) and an upward movement of the upper connector holder (40) is restricted by locating the elevation part seating part (43a) below the upper connector holder support (33).

11. The balloon infuser of claim 9, wherein an upper connector holder coupling part (52) protruding outwards is located at a distal end of an upper side of the upper connector (50), and an upper connector shoulder (53) protruding outwards is located at a distal end of a lower side of the upper connector (50), and
wherein a downward movement of the upper connector (50) is restricted by locating the upper connector stopping step (42) below the upper connector holder coupling part (52) and an upward movement of the upper connector (50) is restricted by locating the upper connector shoulder (53) below the elevation part seating part (43a).

* * * * *